United States Patent
Nayar et al.

(10) Patent No.: US 6,463,783 B1
(45) Date of Patent: Oct. 15, 2002

(54) DISC SLIP APPARATUS

(75) Inventors: Sham S. Nayar, Savage; John G. Gerogeorge, Chanhassen; Rick G. Goodrich, Roseville, all of MN (US); Ronald D. Fowler, Yukon, OK (US)

(73) Assignee: Seagate Technology LLC, Scotts Valley, CA (US)

( * ) Notice: Subject to any disclaimer, the term of this patent is extended or adjusted under 35 U.S.C. 154(b) by 0 days.

(21) Appl. No.: 09/426,920

(22) Filed: Oct. 26, 1999

Related U.S. Application Data

(60) Provisional application No. 60/126,400, filed on Mar. 26, 1999.

(51) Int. Cl.⁷ ............................................. G01N 19/02
(52) U.S. Cl. ................................................ 73/9
(58) Field of Search .................................. 73/9

(56) References Cited

U.S. PATENT DOCUMENTS

| | | | |
|---|---|---|---|
| 5,097,696 A | * | 3/1992 | Le Compagnon ............... 73/9 |
| 5,142,917 A | * | 9/1992 | Mussini et al. .................. 73/9 |
| 5,859,358 A | * | 1/1999 | Wood et al. ..................... 73/9 |

FOREIGN PATENT DOCUMENTS

| JP | 0045733 | * | 2/1990 | ................... 73/9 |

OTHER PUBLICATIONS

Exhibit A; Drawing of Disc Slip Fixture Testing Device, prior to Mar. 26, 1998, of Seagate Technology, Inc.

* cited by examiner

*Primary Examiner*—Robert Raevis
(74) *Attorney, Agent, or Firm*—Westman, Champlin & Kelly, P.A.

(57) ABSTRACT

A disc slip tester for testing disc slip. The tester including a load actuator and load sensor for supplying and measuring test loads. A processor is coupled to the load sensor and is programmed to determine disc slip. Disc slip data is outputted for quality control and performance analysis. A method for analyzing disc slip including supplying a load to a disc in a disc stack and incrementally measuring load and disc displacement and plotting the relationship between load and displacement during test operations.

20 Claims, 16 Drawing Sheets

DISC SLIP APPARATUS

CROSS REFERENCE TO RELATED APPLICATION

The present application claims priority to Provisional Application Ser. No. 60/126,400, filed Mar. 26, 1999, entitled "UNIVERSAL DISC SLIP TESTER".

FIELD OF THE INVENTION

The present invention relates to disc drives. In particular, the present invention relations to a disc slip apparatus for a disc stack of a disc drive.

BACKGROUND OF THE INVENTION

A disc stack includes a plurality of discs clamped to a hub of a spindle motor. Discs are clamped to the hub with sufficient clamping force to limit slip or movement of the discs during operation and handling of the disc drive. Disc clamps are designed to provide sufficient clamping force to limit disc slip for normal operating loads and shock.

Measurement of disc slip force is useful for quality control on an assembly line as well as design analysis. Prior apparatus for simulating loads and measuring disc slip force were not well suited for testing a large sample lot for quality control and "pass-fail" analysis relative to product specifications or disc slip performance standards. Nor were prior test apparatus particularly adaptable for varied testing parameters for design performance evaluation nor establishing standards for clamp force and slip force. The present invention addresses these and other problems, and offers other advantages over the prior art.

SUMMARY OF THE INVENTION

The present invention relates to a disc slip tester for measuring and analyzing disc slip. The tester includes a load actuator and load sensor for supplying and measuring test load. A processor is coupled to the load sensor and is programmed to determine disc slip. Disc slip data is outputted for quality control and performance analysis. The disc slip tester includes a user interface for controlling operating parameters for individual test control for design and performance analysis.

DETAILED DESCRIPTION OF THE PREFERRED EMBODIMENTS

Figure 1:
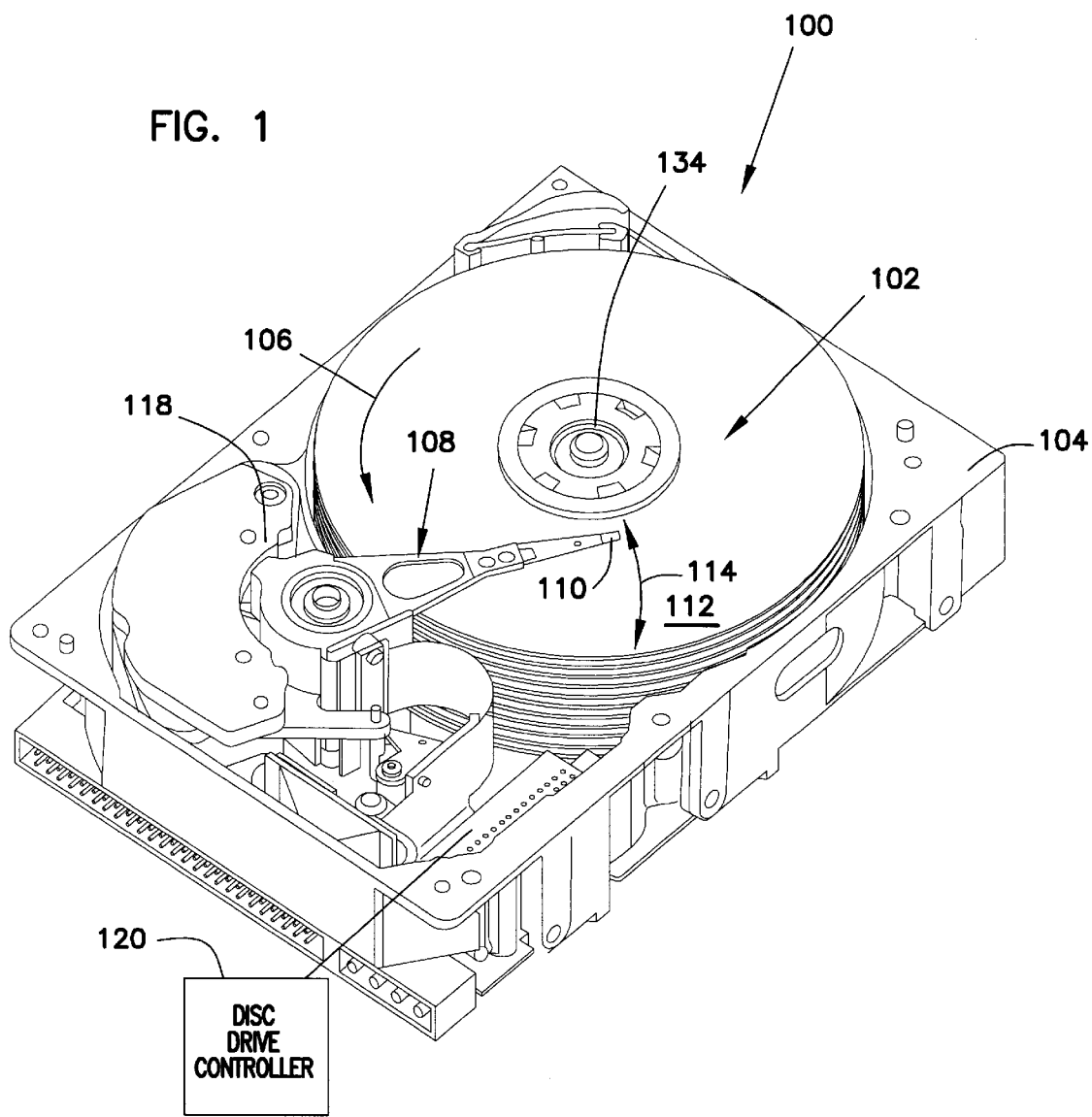
FIG. 1 is a perspective-view of a disc drive.

FIG. 1 illustrates an embodiment of a magnetic disc drive 100 including a disc stack 102 rotationally supported relative to chassis 104 as illustrated by arrow 106. Disc stack 102 is rotated via a spindle motor (not shown). Actuator block 108 supports heads 110 for reading and writing data to discs 112 in the disc stack 102. Actuator block 108 moves as illustrated by arrow 114 by operation of voice coil motor 118 for positioning heads 110 for reading and write operations. Operating components of the drive are coupled to drive circuitry 120.

Figure 2:
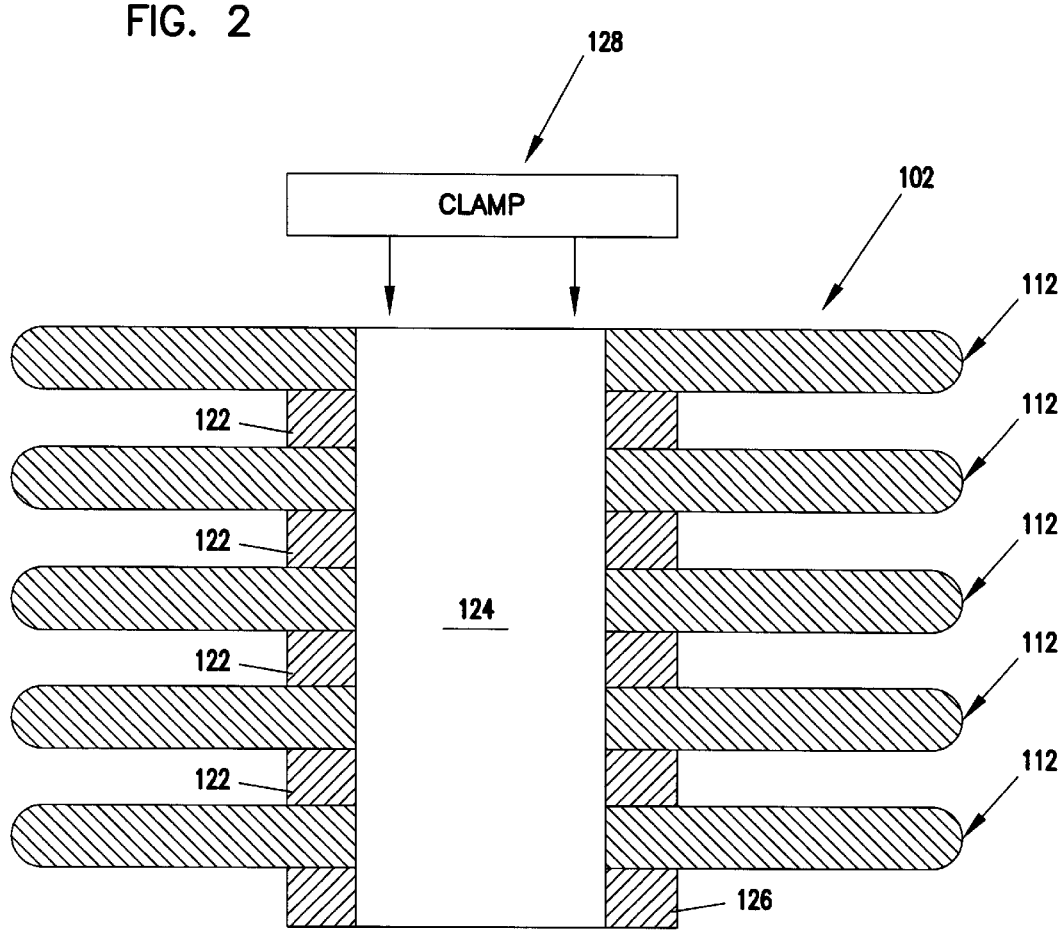
FIG. 2 is a cross-sectional view of a disc stack.

FIG. 2 is a detailed cross sectional view of disc stack 102. As shown, disc stack 102 includes a plurality of discs 112 separated by spacers 122. Discs 112 and spacers 122 are assembled on hub 124 of a spindle motor. Discs 112 are stacked on flange 126 and are separated by spacers 122. A clamp 128 secures discs 112 and spacers 122 on hub 124. Typically clamp 128 is heated to an elevated temperature and is press fit or forced onto hub 124. As the clamp cools, clamp 128 shrinks to provide a clamping force to secure the discs for operation. Alternatively hub 124 is screwed in place with required torque or clamping force. Sufficient clamping force is necessary to secure discs against movement or slip for read and write operations. Shock force to the disc drive during operation or transport can cause disc slip or movement degrading operating performance of the disc drive. Testing and analysis of disc slip can enhance drive design and quality control. The present invention relates to a disc slip apparatus for design and evaluation of and quality control for disc slip for a disc stack.

Figure 3:
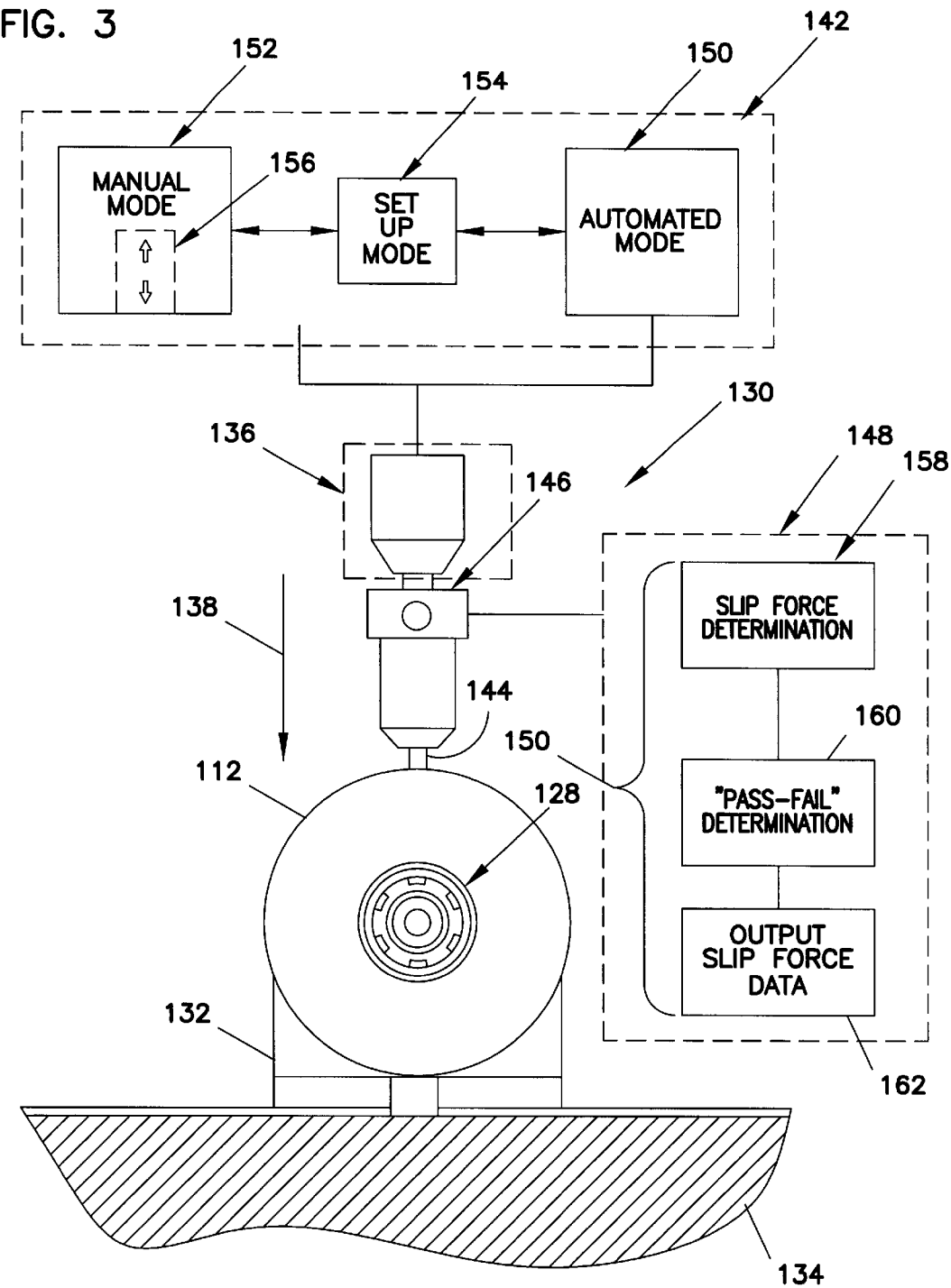
FIG. 3 is schematic illustration of one embodiment of a disc slip tester.

FIG. 3 is an illustration of a disc slip apparatus 130 including a disc stand 132 supported by a base 134 and a load actuator 136 supported relative to the disc stand 132 for supplying a test load as illustrated by arrow 138 to a disc 112 in a disc stack. Load actuator 136 is coupled to a controller 142 for operation. For operation, load is supplied to disc 112 via load. pin 144 coupled to load actuator 136. A load sensor 146 is supported in the load path to measure applied load to the disc 112. Output from load sensor 146 is coupled to processor 148 for determination of disc slip parameters as will be explained.

As shown in FIG. 3, controller 142 includes an automated operation mode 150, a manual operation mode 152 and a set-up mode 154. Test operations can be run in automated mode 150 or manual mode 152. In automated mode, controller 142 operates load actuator 136 to advance load pin 144 at a set velocity to supply a test load to measure disc slip. Operating parameters for the automated mode 150 can be user inputted parameters defined in set up mode 154 or programmed default parameters. Set velocity can be a user set velocity ranging from 0.0001 inches/sec. to 0.01 inches/sec. In the automated mode 150, test load is automatically supplied over a defined test force range for determination of disc slip parameters. In the manual mode, user manually controls operation and advances the push pin 144 in set increments via operation of position keys 156 illustrated diagrammatically to supply a test load. The manual mode provides desired user control for adjusting testing parameters for detailed design and engineering analysis.

As shown in FIG. 3, in the automated mode 150, the processor 148 is programmed to automatically determine disc slip as illustrated by block 158. Disc slip is determined based upon a drop in load force. Processor 148 is also programmed to compare the measured disc slip 158 to a nominal or specification slip force for "pass-fail" determination as illustrated by block 160, which is outputted as illustrated by block 162. If the tested slip force is equal or more than the nominal slip force, the disc stack meets specification standards and a "pass" notice is displayed. If the tested slip force is below the nominal slip force, then the disc stack does not meet specification standards and a "fail" notice is displayed.

Figure 4:
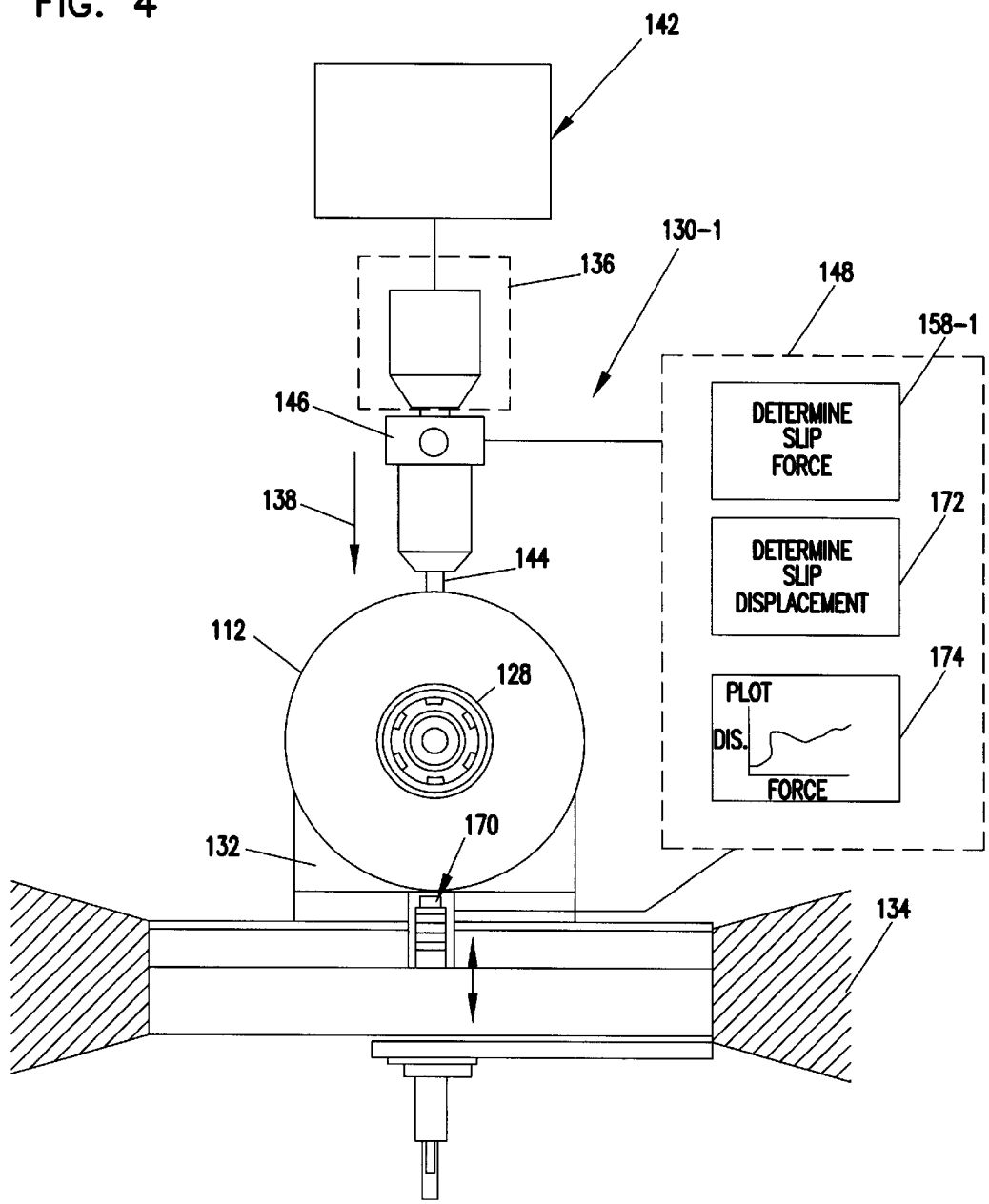
FIG. 4 is schematic illustration of another embodiment of a disc slip tester.

In FIG. 4, disc slip apparatus 130-1 includes a displacement sensor 170 positioned below disc stand 132. Thus, as shown in FIG. 4, load pin 144 contacts an upper surface of a supported disc and displacement sensor 170 contacts a lower opposed surface of test disc 112 to measure disc slip displacement. Since displacement is measured on the lower surface opposite from the load pin 144, the displacement measurement from sensor 170 is a more accurate measurement of disc slip, since indentation of the disc is not included in the measured displacement. Output from load sensor 146 and displacement sensor 170 is downloaded to processor 148. The processor 148 is programmed to determine disc slip 158-1 based upon a drop in load force when dy/dF (where y is the displacement and F is the Force) is negative due to a drop in force. The processor 148 determines disc slip displacement based upon output from displacement sensor 170 as illustrated by block 172.

Data from load sensor 146 and displacement sensor 170 is plotted live in real time during test operations for disc slip analysis as illustrated by block 174. Load and displacement date is saved to a data file for further use an analysis. The slip force vs. displacement plot can be rescaled or resized upon completion of a test cycle for display.

For real time plots, load sensor 146 is a compression load cell having a calibrated measurement scale between 0–10 volts to limit noise and displacement sensor 170 is a linear displacement transducer (LVDT) calibrated for a measurement scale between 0–10 volts to limit noise. In one embodiment, load cell is a Sensortec Compression load cell available from Sensortec of Columbus, Ohio. LVDT preferably includes a vacuum retract and is available from Solitron. Processor 148 is a CIODAS08 computer board available from Computer Board, Inc. of Mansfield, Mass., 02040, for rapid analog signal processing for real time graphic capabilities. Output from load sensor 146 is amplied by in-line amplifier provided by Sensodic. Displacement sensor 170 is amplified for processing via an amplifier available from Lusas Control Systems Products of Hampton, Va.

Figure 5:
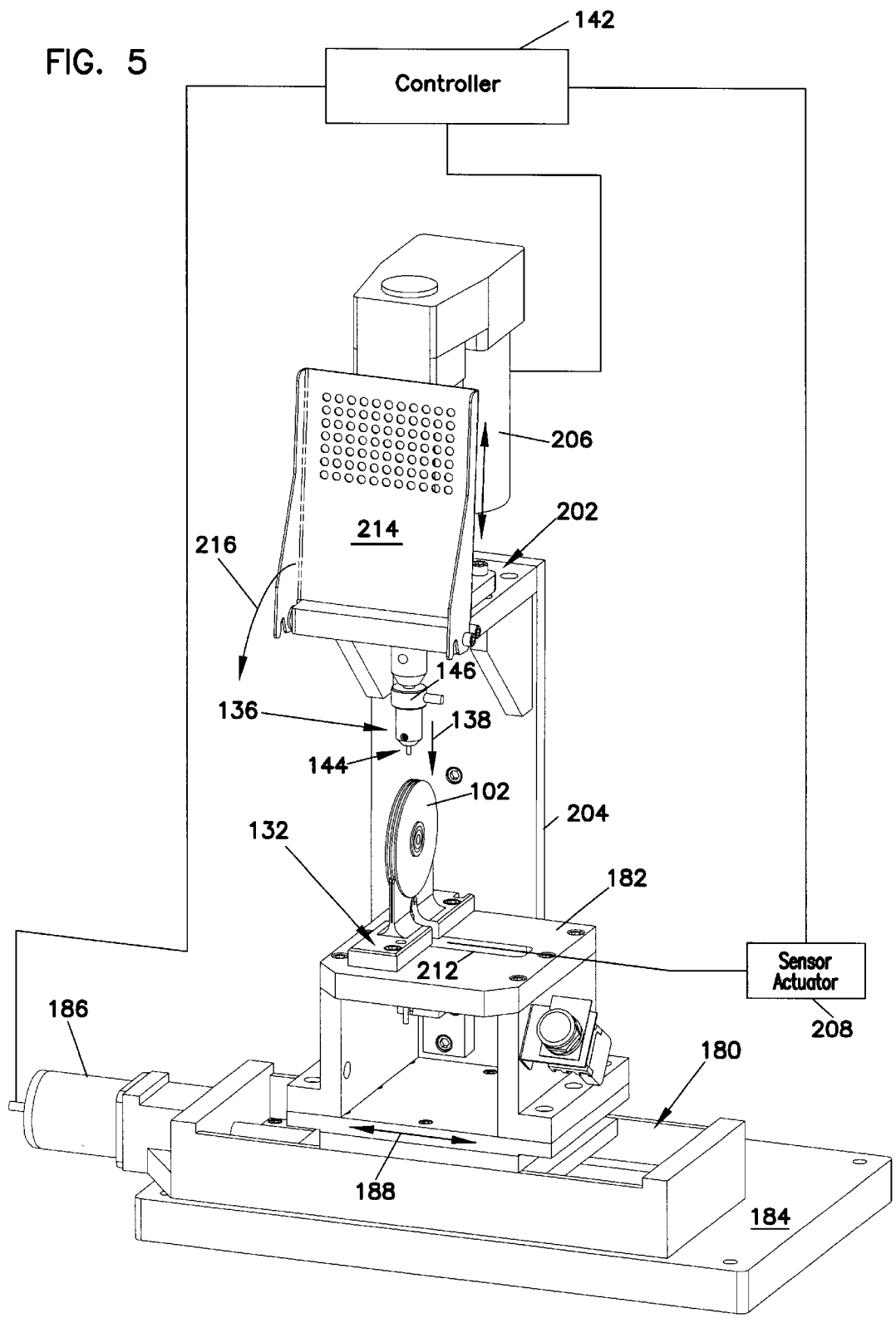
FIG. 5 is a perspective illustration of an embodiment of a disc slip tester.
Figure 6:
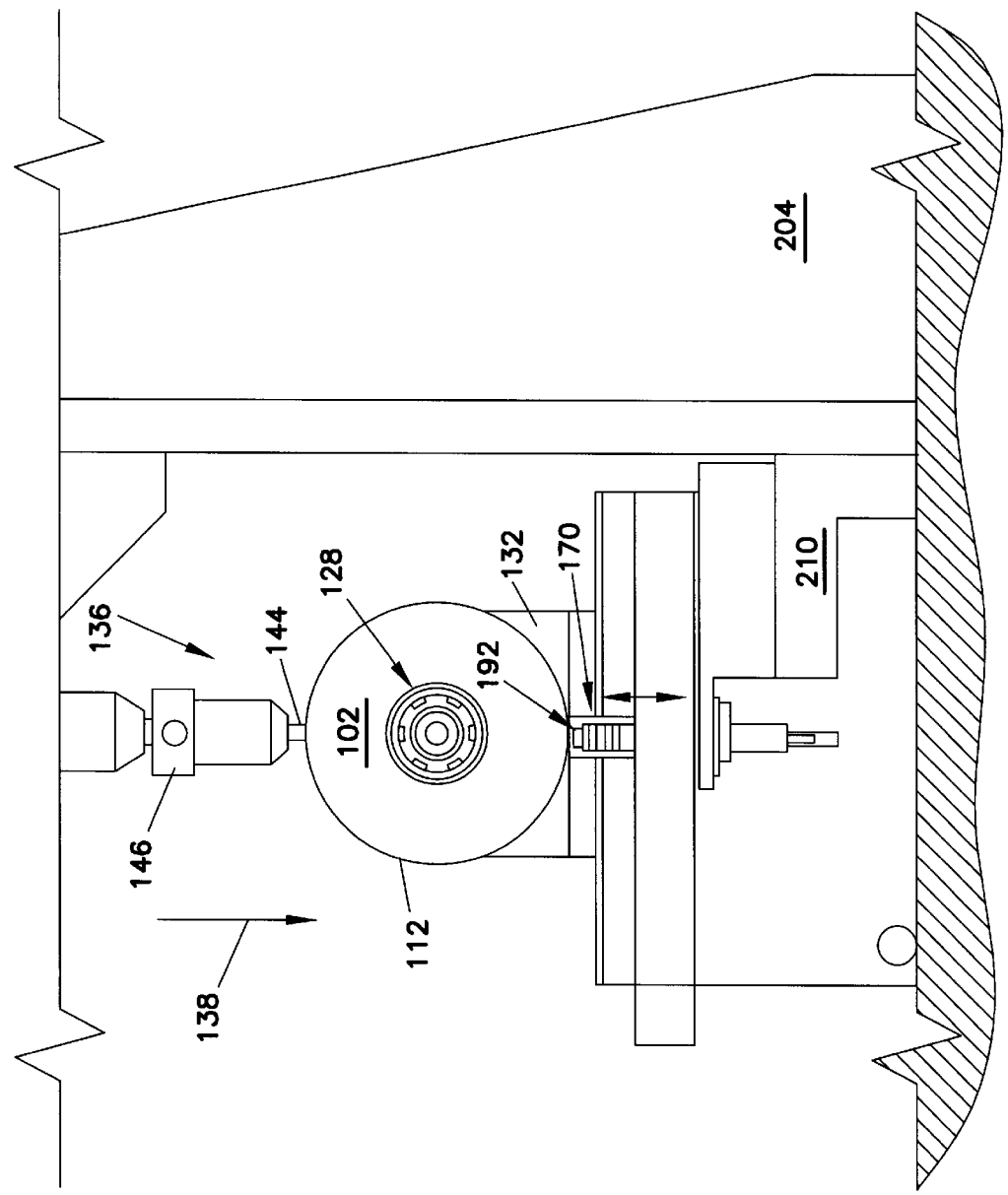
FIG. 6 is an alternate view of the tester apparatus of FIG. 5.

FIGS. 5–6 illustrate test apparatus with a load/unload slide 180. Slide 180 movably supports a disc stand platform 182 relative to a base plate 184. Disc stand 132 is coupled to disc stand platform 182 and movable therewith. A slide drive 186 is coupled to slide 180 to move slide 180 between a retracted home position and an operating or test position (shown) as illustrated by arrow 188. Slide 180 is supported in the retracted home position out of alignment with load actuator 136 and displacement sensor 170 prior to and after testing operations for loading and unloading a disc stack. For operation, slide 180 is moved to the test position as illustrated by arrow 188 by slide drive 186 to position the disc stack in axial alignment with the load pin 144 and a sensor tip-192 (as shown in FIG. 6) of displacement sensor 170.

Load actuator 136 is supported above stand platform 182 by load platform 202 connected to base plate 184 via post 204. Load actuator 136 includes a drive motor 206 which operates to move pin 144 from a retracted position (shown in FIG. 5) to test position 160 (shown in FIG. 6). For test operations, drive motor 206 moves pin 144 downwardly as illustrated by arrow 138 to supply a test load. Sensor tip 192 is movable between a retracted home position (not shown) and an extended test position by sensor actuator 208 to contact the disc edge for displacement measurements during test operations. In the embodiment shown, drive motor 206 is a linear stepper motor. Operation of drive motor 206, slide drive 186, and sensor actuator 208 is coordinated by controller 142

As illustrated in FIG. 5, displacement sensor 170 is an LVDT with vacuum retract to operate between the retracted home position and the extended test position. The LVDT is supported by bracket 210 coupled to base plate 184 and in the extended position tip 192 of sensor 170 extends through a platform opening 212 (shown in FIG. 5) to contact an edge surface of a supported disc for displacement measurement. In the retracted home position, tip 192 is retracted from the disc stack for positioning a disc in alignment with load pin 144 and sensor tip 192 for test operation. During operation, a cover 214 is closed as illustrated by arrow 216 for safety.

Figure 7:
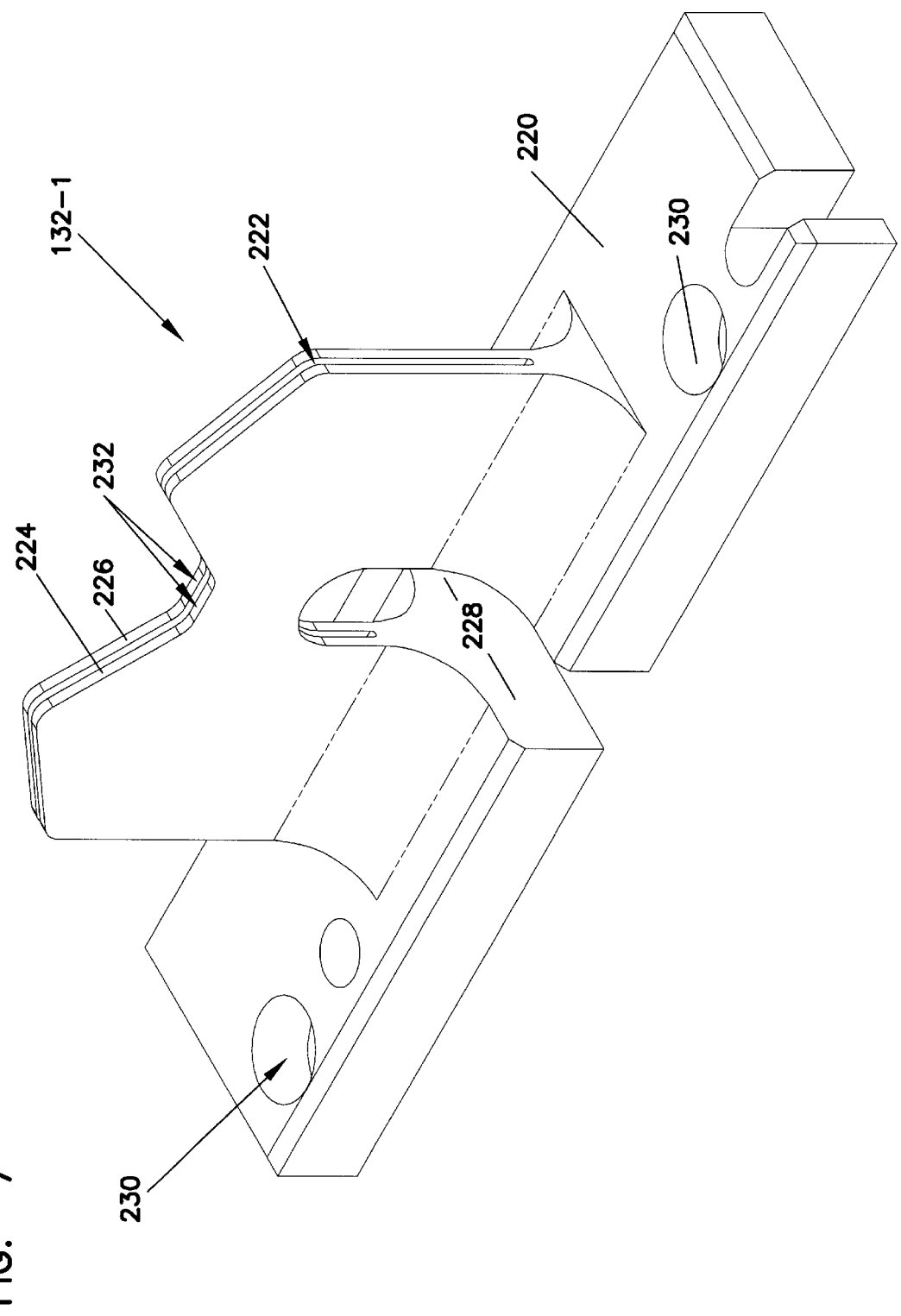
FIG. 7 is a perspective illustration of an embodiment of a disc stand.
Figure 8:
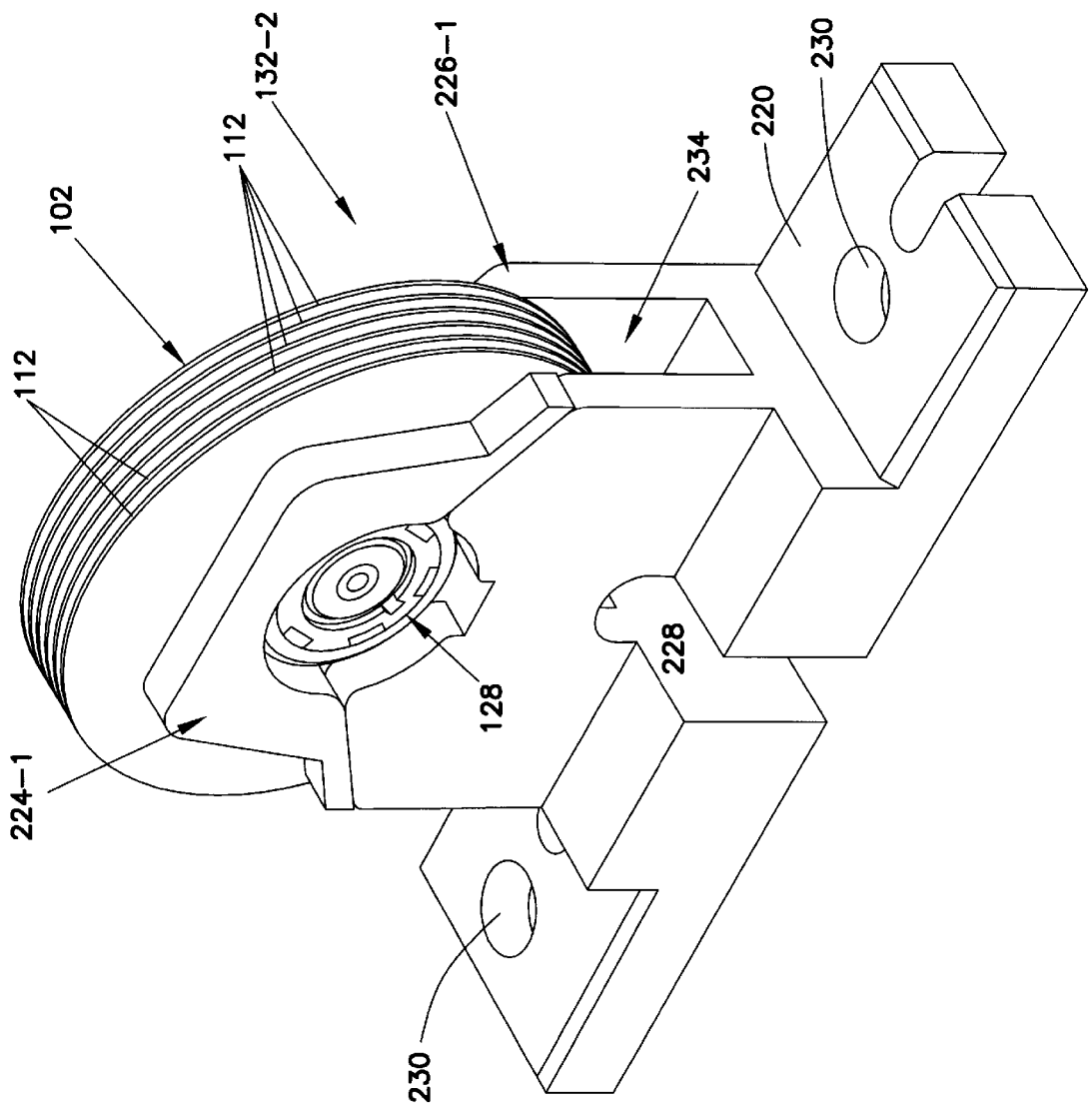
FIG. 8 is a perspective illustration of another embodiment of a disc stand.

FIGS. 7–8 illustrate alternate embodiment disc stands 132-1, 132-2. FIG. 7 illustrates a disc stand 132-1 for single disc support including base 220, single disc slot 222, first and second upright supports 224, 226, and sensor channel 228. Base 220 is coupleable to stand platform 182 by fastener holes 230. A test disc is inserted into disc slot 222 and disc stack 102 is supported via spacers on opposed sides of the disc in disc slot 222. Spacers contact and are supported on "V" shaped seat 232 formed by upright supports 224, 226. Disc slot 222 is opened to sensor channel 228 so that when disc stand 132-1 is in the test position, LVDT contacts a lower edge of a supported disc for displacement measurement. For operation, load is supplied to the disc in slot 222 for disc slip measurement relative to spacers.

An alternate disc stand 132-2 for multidisc support is illustrated in FIG. 8 where similar numbers are used to identify similar parts. Disc stand 132-2 includes a disc stack slot 234 opened to sensor channel 228 for contacting a test disc with LVDT or displacement sensor 170 and spaced first and second upright supports 224-1, 226-1. First upright support 224-1 supports a first end of the disc stack and second upright support 226-1 supports a second end. In particular, support 224-1 engages and supports clamp 128 of disc stack 102 and support 226-1 supports flange 126. Selected discs 112 of the supported disc stack 102 are aligned relative to load pin 144 for test operations as will be explained. Load is supplied to discs in the disc stack for disc slip measurement relative to hub 124.

For test operations for a multi-disc stand 132-2 controller 142 is programmed to move the slide 180 to a specified disk position to align a particular disc relative to push pin 144 for testing. For example, a system prompt can request a disk number to be tested and if in response to the prompt, Disc No. 2 is entered, controller 142 operates slide 180 to move the stand 132-2 to the align the selected Disc. No. 2 with the push pin 144. Alternatively, the disc number to be tested can be programmed into the controller 142. The elevation of tip 192 of LVDT is based upon the disc stack type and size. Prior to operation, a user identifies disc stack type and controller 142 is programmed to raise sensor tip 192 and lower push pin 144 to the proper test elevation (or test position) for commencement of disc slip measurement.

Figure 9:
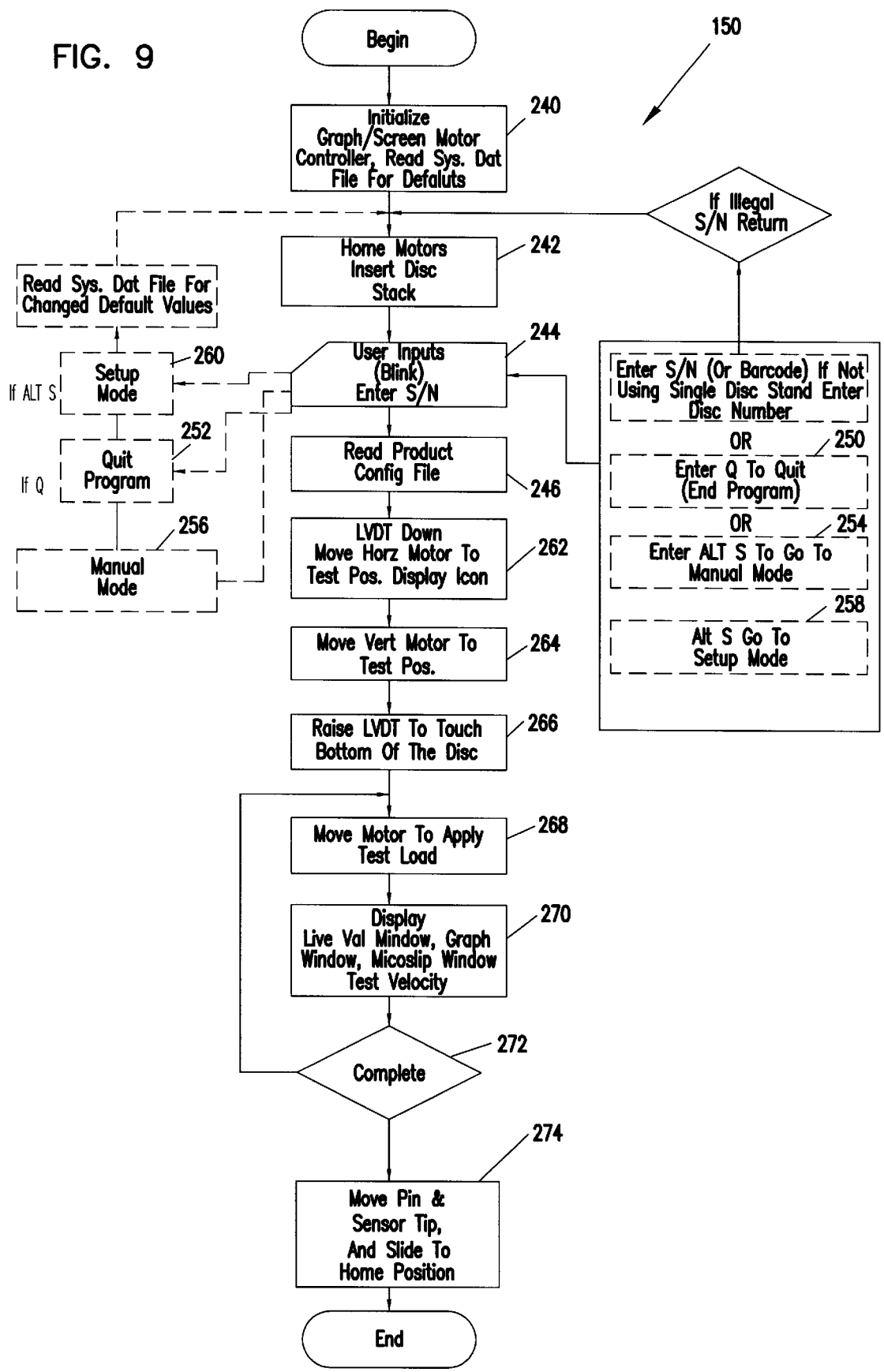
FIG. 9 is a flow chart for operation of an embodiment of a disc slip tester.

FIG. 9 illustrates an operating embodiment for automated operating mode 150. Controller includes a computer executable operating program with programmed operating instructions and display. As illustrated in FIG. 9, the operating program is initialized as illustrated by block 240. For initialization the default operating parameters (for example set velocity) are read from a data file. For test operations, slide drive 186 and drive motor 206 are reset to retracted home positions and an operator inserts a disc stack 102 into stand 132 in the retracted position out of alignment with load pin 144 and displacement sensor 170 as illustrated by block 242. The program prompts a user to input a serial number or product identification code for the disc stack 102 loaded into the disc stand as illustrated by block 244.

In the automated mode 150, the apparatus of the present invention is adapted for testing disc stack types with different product specifications. As shown in block 246, the system reads operating parameters for the disc stack type being tested for commencing disc slip test measurements. Program operations can be ended as illustrated by blocks 250, 252 or program control can be switched to manual operation mode 152 as illustrated by blocks 254, 256 or set up mode as illustrated by blocks 258, 260 as will be explained in detail.

For operation in the automated mode 150, the LVDT is retracted, and the slide 180 moves disc stand 132 to the test position as illustrated by block 262. The pin 144 is actuated (or lowered to) the test position proximate to the disc to be tested by motor 206 as illustrated by block 264. The LVDT 170 is raised to contact the test disc as illustrated by block 266. Thereafter, pin 144 is advanced at the set velocity to apply a test load to measure disc slip as illustrated by block 268. Disc slip parameters are displayed as illustrated by block 270. Load is supplied to the disc for a test operation until the test operation is complete as illustrated by block 272. Upon completion of the test, pin 144 and sensor tip 192 are retracted and slide 180 is moved to the retracted home position to unload the tested disc stack as illustrated by blocks 274.

Figure 10:
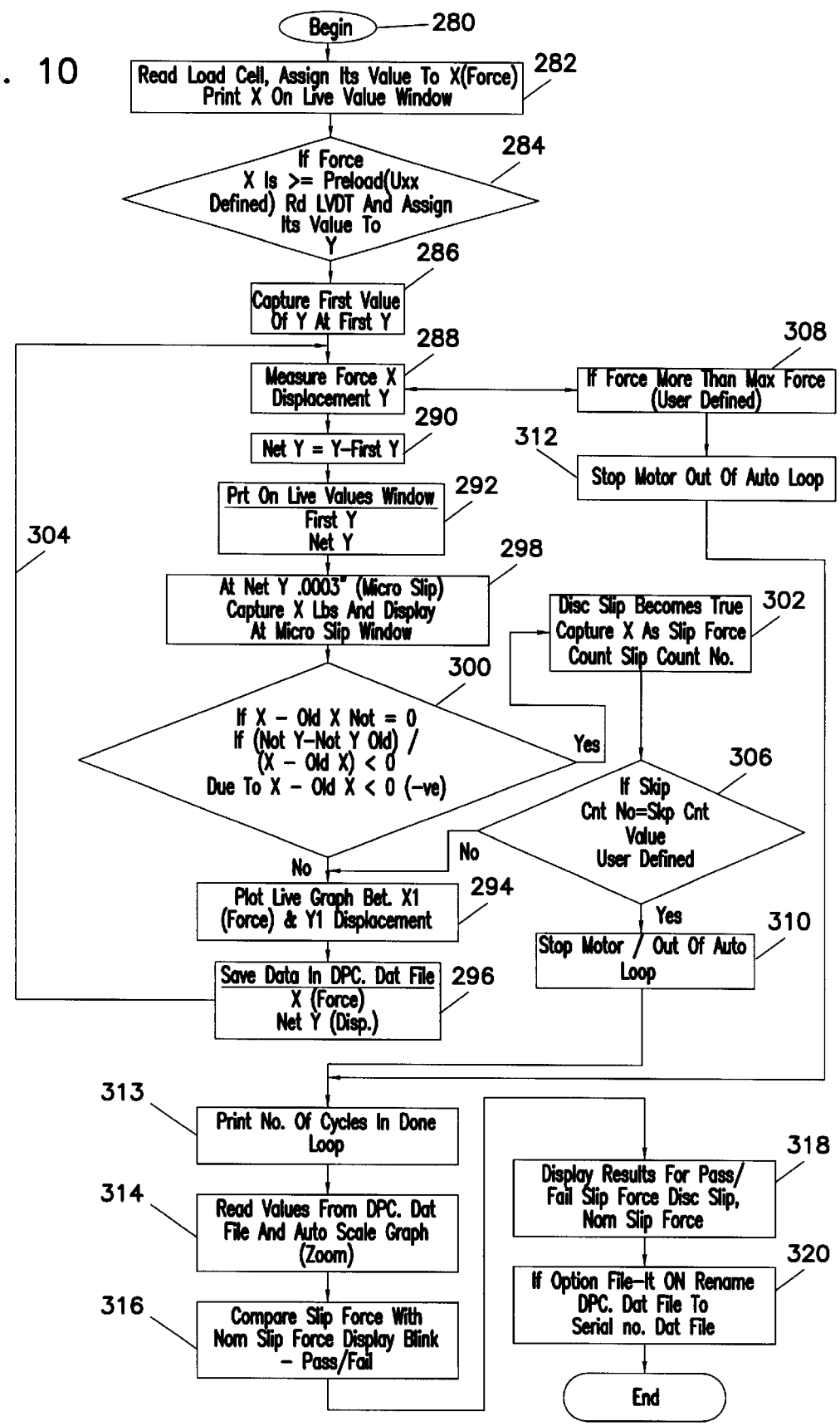
FIG. 10 is a flow chart of an operation embodiment for measuring and determining disc slip parameters.

During test operations, processor 148 calculates disc slip parameters (for example, disc slip force and disc slip displacement) as illustrated in FIG. 10. Operation begins as illustrated by block 280 and the applied load is read from the load sensor as illustrated by block 282. Once the pre-load force is supplied to the disc as illustrated by block 282, the position of the LVDT is initialized to calculate net displacement based upon movement of the LVDT pin relative to the initial position of the LVDT pin as illustrated by block 286. In the embodiment illustrated the pre-load force is 9 lbs.

For test operation, force and displacement are measured as illustrated by block 288. Net displacement is calculated based upon measured displacement minus initial displacement, as illustrated by block 290. Measured force and displacement values are displayed as illustrated by block 292 during test operation and plotted on a Force vs. Displacement graph as illustrated by block 294. Measured force and displacement data is saved to a data file as illustrated by block 296. In a preferred embodiment, processor 148 determines microslip force (preferably at 0.0003 inches slip) which is outputted to a display terminal or saved to a data file for performance analysis as illustrated by block 298.

As previously explained, processor 148 is programmed to determine disc slip as illustrated by block 300. The processor 148 is programmed to determine disc slip based upon a drop in load force when dy/dF (where y is the displacement and F is the Force) is negative due to a drop in force. The processor 148 totals the number of disc slips (or slip count) as illustrated by block 302. Test operation and measurement continues as illustrated by line 304 until slip count reaches maximum slip count value 306 or the applied force equals the maximum load as illustrated by block 308 and test operation is ended as illustrated by blocks 310, 312. The maximum slip count or maximum test load can be user defined or a default operation parameter.

After test operation is complete, test summary data is displayed. In the embodiment illustrated in FIG. 10, the test summary display includes the number of measurements as illustrated by block 313. The force vs. displacement graph is rescaled so that the graph data fills the display window as illustrated by block 314. The measured slip force is compared to the nominal or specification slip force as previously explained and a "pass/fail" notice is displayed as illustrated by block 316. Summary test data is displayed as illustrated by block 318. Measured data can be saved to a permanent data file as illustrated by block 320.

Figure 11:
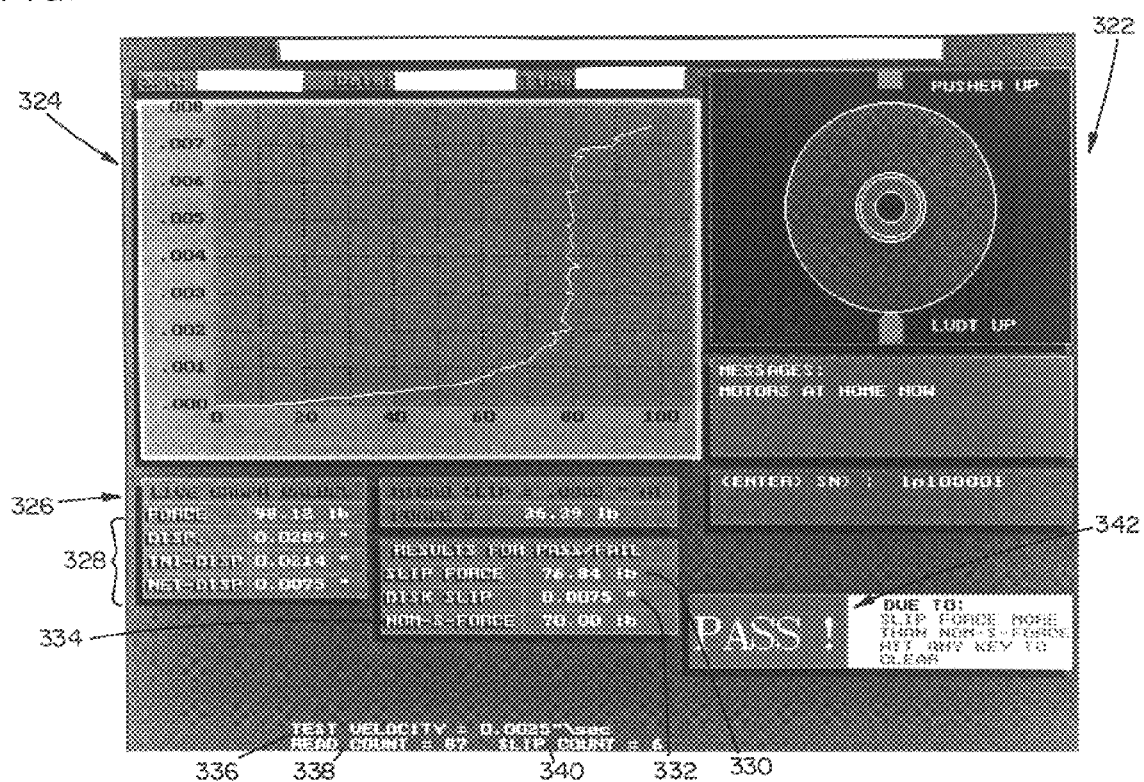
FIG. 11 is an embodiment of a screen display for displaying disc slip parameters.

FIG. 11 is an embodiment of a program display 322 including Force vs. Displacement graph 324. Numerical values for force 326, displacement 328, slip force 330, disc slip displacement 332, nominal disc slip 334, test velocity 336, number of measurement cycles 338 and number of disc slips (or disc slip count) 340 are also displayed. A "pass/fail" notice 342 is also displayed as previously explained.

Figure 12:
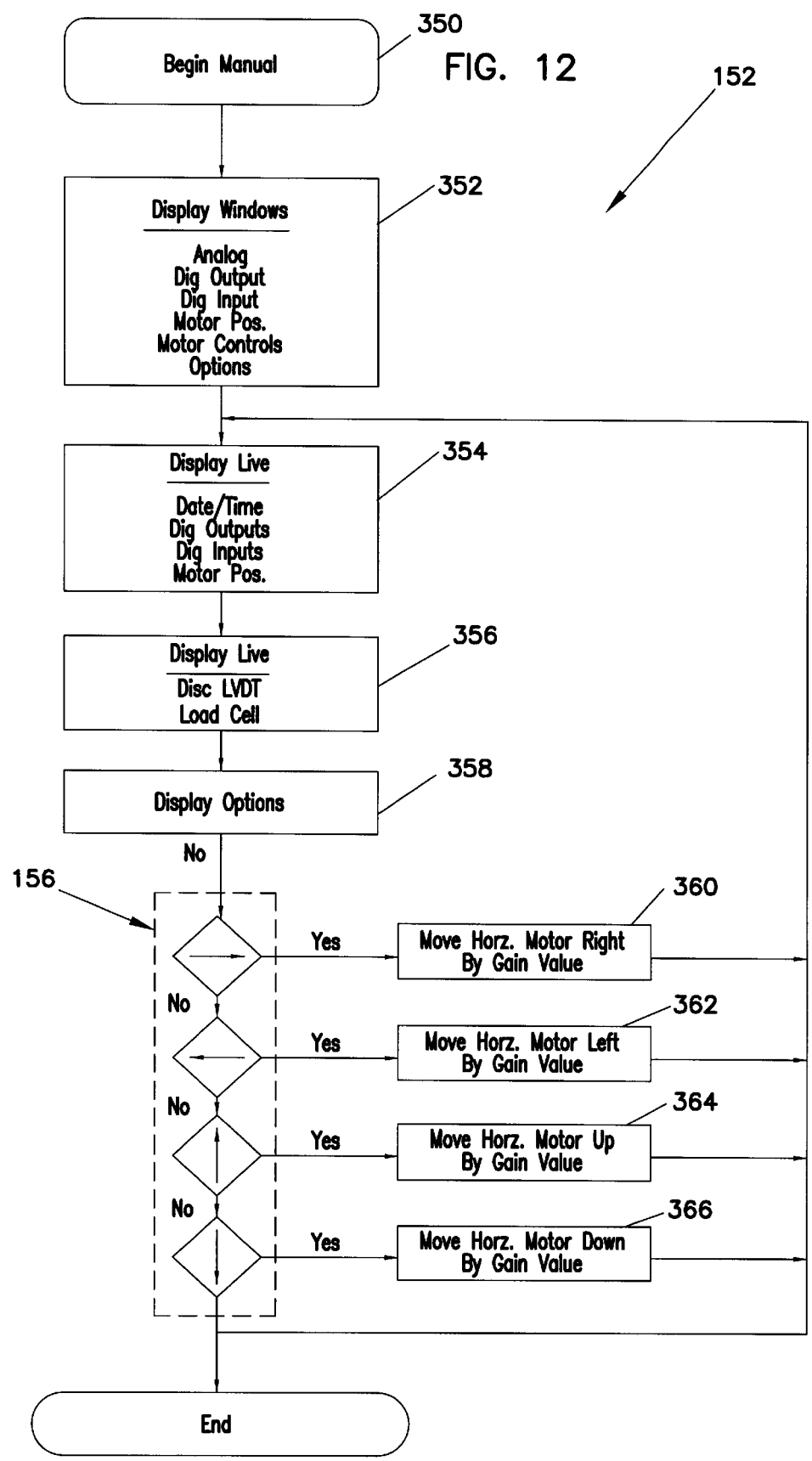
FIG. 12 is flow chart of a manual operation embodiment for a disc slip tester.
Figure 13:
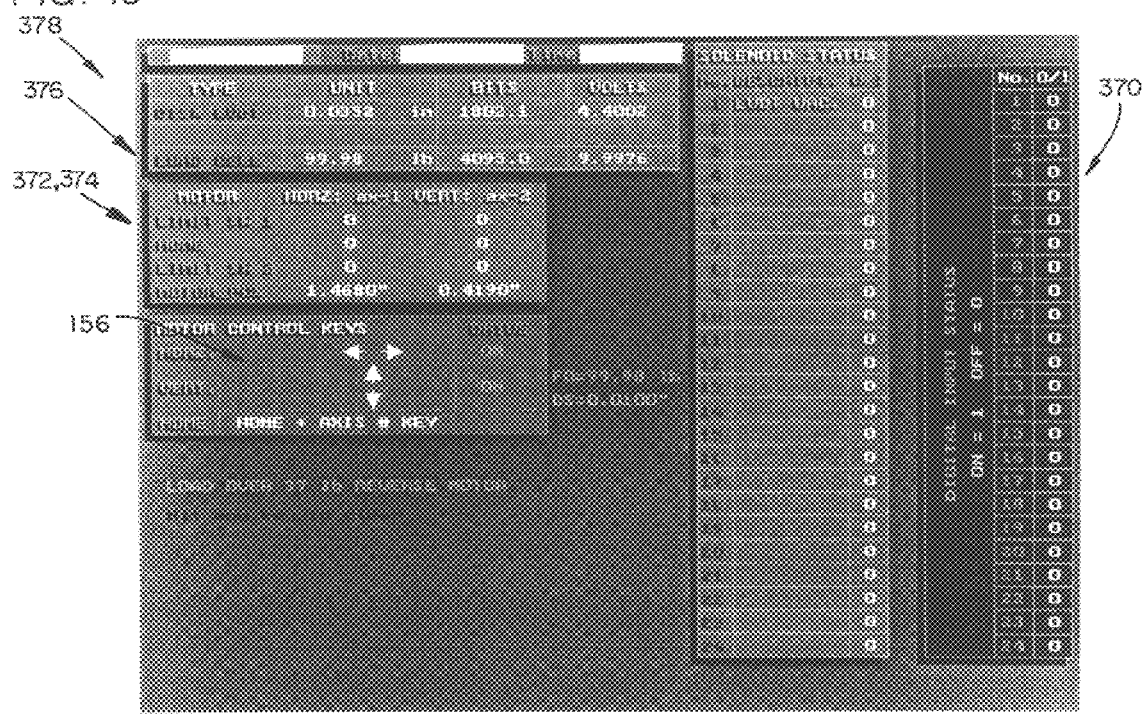
FIG. 13 is an embodiment of a control-screen for manual operation of a disc slip tester.

As previously explained, test operation can proceed in manual mode 152 as illustrated in FIGS. 12–13. Manual operation begins as illustrated by block 350. An operating program displays an operating screen as illustrated by blocks 352, 354, 356, 358. Operating screen displays the position of slide drive 186 and load drive 206, as illustrated by block 354. The operating program also displays load cell 146 and displacement sensor 170 output as illustrated by block 356. Position keys 156 operate slide drive 186 to move slide between a retracted position and a test position in step increments as illustrated by blocks 360, 362 and move load motor 206 in step increments to apply a test load to a supported disc as illustrated by blocks 364, 366. FIG. 13 illustrates an embodiment of a program display 370 for manual mode. As shown, program display 370 displays slide drive 186 and load drive 206 position 372, 374 and output 376, 378 from load cell 146 and displacement sensor 170.

Figure 14:
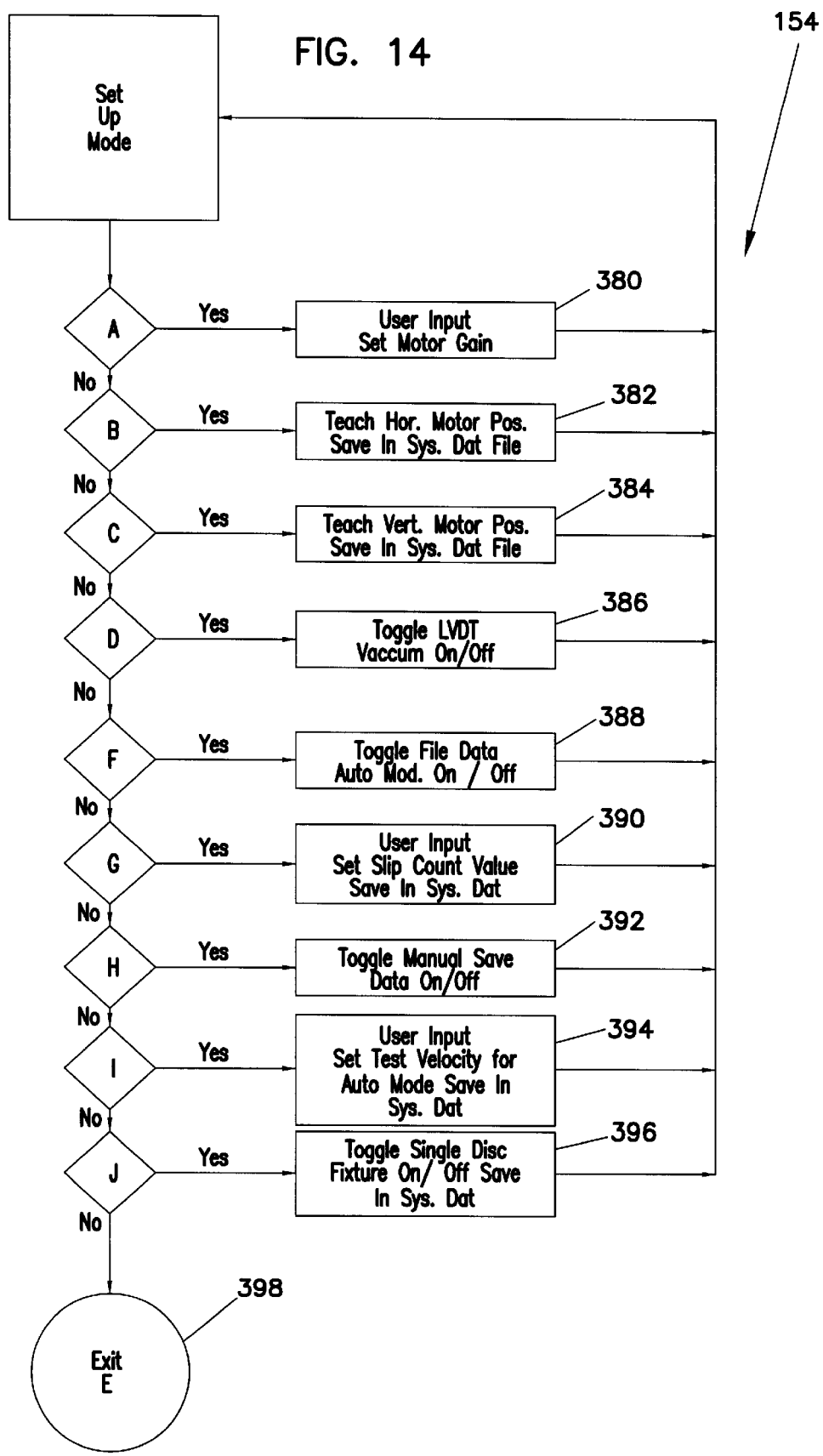
FIG. 14 is a flow chart of an embodiment of a set-up mode for inputting operating parameters for a disc slip tester.
Figure 15:
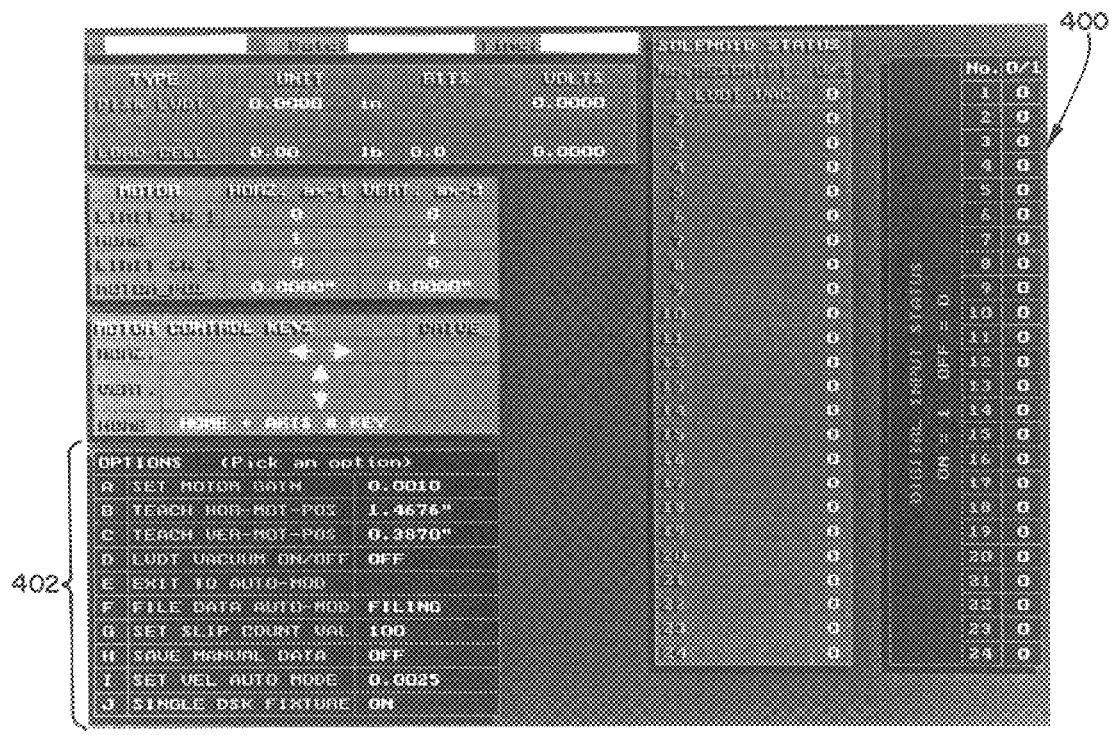
FIG. 15 is an embodiment of a control screen for inputting operating parameters for a disc slip tester.

FIGS. 14–15 illustrate an embodiment of set up mode 154 for entering or changing test operation parameters. In the embodiment shown, user inputted operating parameters include motor gain 380 for manual operation of load motor 206, test-position 382 for slide drive 186, test position 384 for load motor 206 (to position pin 144 at the edge of the disc), toggle control 386 for displacement sensor between a retracted position and a test position, toggle data save in automated mode 388, limit slip count 390, toggle data save-in manual mode 392, set velocity for push pin 144 in automated mode 394 and toggle for disc stand type 396 for slide 180 control. For automated operation, user exits 398 set up mode 150. FIG. 15 illustrates an embodiment of a screen display 400 for inputting parameters 402 for set up mode 152.

Figure 16:
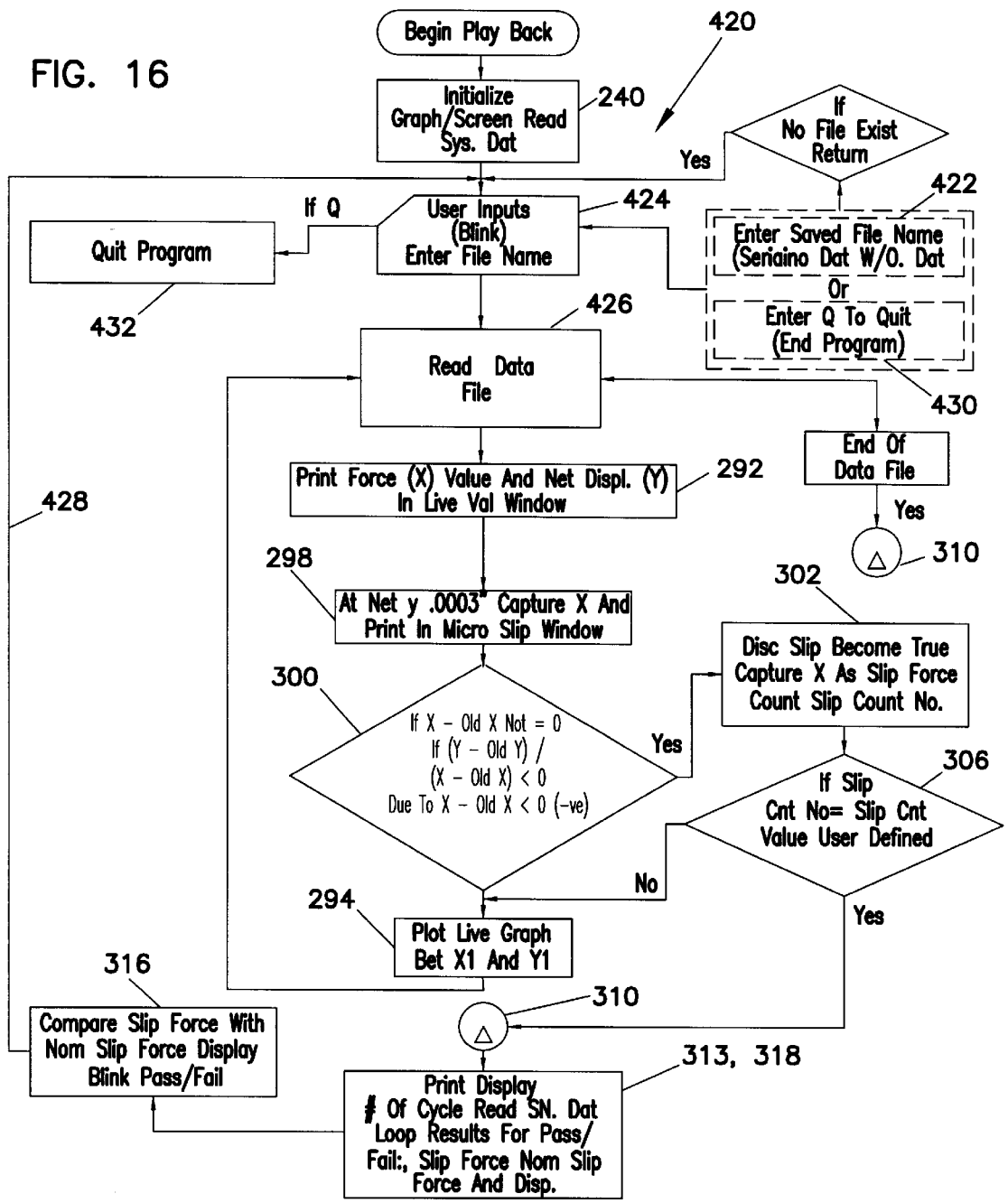
FIG. 16 is a flow chart of an embodiment of a playback mode for a disc slip tester.

Test operations can be saved and previous test operations can be replayed by the program upon completion of a test operation without repeating the physical test cycle of the disc stack for later analysis. Test operations can be replayed in a playback mode 420 as illustrated in FIG. 16. Test operation can be replayed in playback mode 420 by a remote computer without testing equipment. FIG. 16 illustrates an embodiment of playback mode 420, where like numbers are used to identify like operation steps in FIGS. 9–10. To initiate playback operation 420, user inputs a saved data file from a previous test operation as illustrated by blocks 422, 424. The program reads the data file as illustrated by block 426 and displays the data as previously explained and illustrated by blocks 292, 298. The program in playback mode 420 also performs disc slip calculations 300 and displays a force vs. displacement graph 294. Upon completion of the playback of test data as illustrated by block 310, the program displays test results as illustrated by blocks 313, 316, 318. Playback operation continues as illustrated by line 428 until ended as illustrated by blocks 430, 432.

Thus as described, the disc slip apparatus of the present invention includes a base 134 and a disc stand 132 supported by the base. A disc is supported by disc stand 132 and a load actuator 136 supplies a load to a disc supported by the disc stand. A load sensor 146 measures applies load and a computer 148 is coupled to the load sensor 146 and is programmed to determine disc slip.

It is to be understood that even though numerous characteristics and advantages of various embodiments of the present invention have been set forth in the foregoing description, together with details of the structure and function of various embodiments of the invention, this disclosure is illustrative only, and changes may be made in detail, especially in matters of structure and arrangement of parts within the principles of the present invention to the full extent indicated by the broad general meaning of the terms in which the appended claims are expressed. For example, the particular elements may vary depending on the particular application for a disc stack while maintaining substantially the same functionality without departing from the scope and spirit of the present invention. In addition, although the preferred embodiment described herein is directed to a magnetic disc drive system, it will be appreciated by those skilled in the art that the teachings of the present invention can be applied to other systems, for example, an optical disc drive system, without departing from the scope and spirit of the present invention.

What is claimed is:

1. A disc slip apparatus comprising:
   a base;
   a disc stand supported by the base;
   a load actuator supportably coupled to the base to supply an input load to a disc supported by the disc stand;
   a load sensor interposed in a load path relative to the disc supported by the disc stand; and
   a computer coupled to the load sensor and adapted to receive a first force measurement at a first input force and a second force measurement at a second input force and the computer programmed to determine disc slippage based upon a comparison of the first and second force measurements to determine disc slip force.

2. The disc slip apparatus of claim 1 wherein the disc slippage is determined based upon a force drop between the first force measurement and the second force measurement to determine the disc slip force.

3. The disc slip apparatus of claim 1 wherein the computer includes a "pass-fail" output based upon the determined slip force compared to set slip force parameters.

4. The disc slip apparatus of claim 1 including a displacement sensor, wherein the load actuator supplies the input load to a disc in a first direction and the displacement sensor is positioned in an opposed direction to measure disc slip displacement.

5. The disc slip apparatus of claim 4 wherein output from the load sensor and the displacement sensor is coupled to the computer and the computer is programmed to plot a relationship between the measured force and the measured displacement.

6. The disc slip apparatus of claim 5 wherein the computer is programmed to plot the relationship of the measured force and the measured displacement in real time during incremental application of the input force by the load actuator.

7. The disc slip apparatus of claim 5 wherein the computer is programmed to save force and displacement data to a data file and the apparatus includes a playback mode to replot the relationship between the measured force and the measured displacement.

8. The disc slip apparatus of claim 5 wherein the computer is programmed to rescale the force and displacement plot.

9. The disc slip apparatus of claim 1 wherein the load actuator is coupled to a controller and the controller is programmed for selective operation in an automated mode where the load actuator supplies the input load at a set velocity and a manual mode to allow user controlled operation of the load actuator.

10. The disc slip apparatus of claim 1 wherein the load actuator is coupled to a controller and is operable in an automated mode having at least one user programmable operating parameter and operably in the automated mode to supply a plurality of incremental input forces to the disc supported by the disc stand.

11. The disc slip apparatus of claim 10 wherein the at least one user programmable operating parameter includes load actuator velocity to define the incremental input forces supplied to the disc.

12. The disc slip apparatus of claim 1 wherein the load actuator is coupled to a controller and is operable in a manual mode via position keys programmed to incrementally operate the load actuator to supply incremental input forces to the disc supported by the disc stand.

13. The disc slip apparatus of claim 12 wherein an operating increment for the position keys is user programmable.

14. A disc slip apparatus comprising:
   a load actuator to supply a load to a disc in a disc stack; and
   means for determining disc slip and disc slip force based upon the load supplied by the load actuator.

15. The disc slip apparatus of claim 14 wherein the means for determining disc slip force includes a load sensor in series with the-load actuator and a displacement sensor in an opposed position for measuring disc slip displacement.

16. A method for analyzing disc slip comprising steps of:
   a) loading a disc stack into a disc stand;
   b) supplying an input load to a disc in the disc stand;
   c) incrementally measuring load in a load path to the disc;
   d) incrementally measuring disc displacement; and
   e) incrementally plotting a relationship between the measured load and the measured displacement during a test operation.

17. The method of claim 16 further comprising:
   f) processing the incrementally measured loads to determine disc slip.

18. The method of claim 16 wherein the input load is incrementally supplied at a set velocity.

19. The method of claim 17 wherein the step of processing the incrementally measured loads includes the step of comparing the incrementally measured loads to determine a force drop to determine a disc slip force.

20. A disc slip apparatus comprising:

a base;

a disc stand supported by the base;

a load actuator coupled to the base to supply an input load to a disc supported by the disc stand;

a load sensor interposed in a load path to the supported disc; and a displacement sensor coupleable to the support disc in the load path.

* * * * *